(12) United States Patent
Meindl et al.

(10) Patent No.: US 9,428,345 B2
(45) Date of Patent: Aug. 30, 2016

(54) APPARATUS FOR SEPARATING SPHERICAL OR CYLINDRICAL OBJECTS

(71) Applicant: Siemens Healthcare Diagnostics Products GmbH, Marburg (DE)

(72) Inventors: Josef Meindl, Eschborn (DE); Hugo Wilmes, Bad Soden (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 53 days.

(21) Appl. No.: 14/298,202

(22) Filed: Jun. 6, 2014

(65) Prior Publication Data

US 2015/0014342 A1 Jan. 15, 2015

(30) Foreign Application Priority Data

Jul. 8, 2013 (EP) ..................................... 13175470
Jul. 30, 2013 (EP) ..................................... 13178460

(51) Int. Cl.
*B65G 47/14* (2006.01)
*B65G 59/00* (2006.01)
*G07F 11/00* (2006.01)
*B65G 47/57* (2006.01)
*G01N 35/00* (2006.01)
*B01F 13/08* (2006.01)

(52) U.S. Cl.
CPC .......... *B65G 47/57* (2013.01); *B01F 13/0818* (2013.01); *B65G 47/1485* (2013.01); *G01N 35/00* (2013.01); *G01N 2035/00534* (2013.01)

(58) Field of Classification Search
CPC .............. B65G 47/57; B65G 47/1485; B01F 13/0818; G01N 35/00; G01N 2035/00534
USPC ............................................ 221/1, 212, 171
See application file for complete search history.

(56) References Cited

U.S. PATENT DOCUMENTS

| 3,065,841 | A | * | 11/1962 | Stover | ............... | B65G 47/1485 198/392 |
| 3,294,284 | A | * | 12/1966 | Chambers | ........... | G07F 17/0092 221/120 |
| 3,417,542 | A | * | 12/1968 | Merrill | ................... | B65B 35/06 221/182 |
| 3,446,397 | A | * | 5/1969 | Chambers | ............... | B65B 5/103 221/296 |
| 3,448,894 | A | * | 6/1969 | Modrey | .................. | B25B 23/02 221/160 |
| 3,545,164 | A | * | 12/1970 | Middleton | .............. | B65B 5/103 221/156 |

(Continued)

FOREIGN PATENT DOCUMENTS

| DE | 102006061904 A1 | 7/2008 |
| DE | EP 2824047 A1 * | 1/2015 | .......... B01F 13/0818 |

(Continued)

OTHER PUBLICATIONS

European Search Report of European Application No. 14174886.3-1553 dated Aug. 22, 2014.

*Primary Examiner* — Rakesh Kumar
(74) *Attorney, Agent, or Firm* — Dugan & Dugan, PC

(57) ABSTRACT

An apparatus for separating rod-like or spherical agitating elements in an automatic analyzer allows quick and error-resistant separation and automated charging of cuvettes with the agitating elements. For this purpose, it comprises a lever provided with a bore, wherein the bore is configured such that it can accommodate one of the agitating elements. The bore, in a first position of the lever, is arranged beneath an entry opening and, in a second position of the lever, is arranged above an exit opening, wherein the lever, in the second position, closes the entry opening.

18 Claims, 5 Drawing Sheets

(56) References Cited

U.S. PATENT DOCUMENTS

Figure 1:
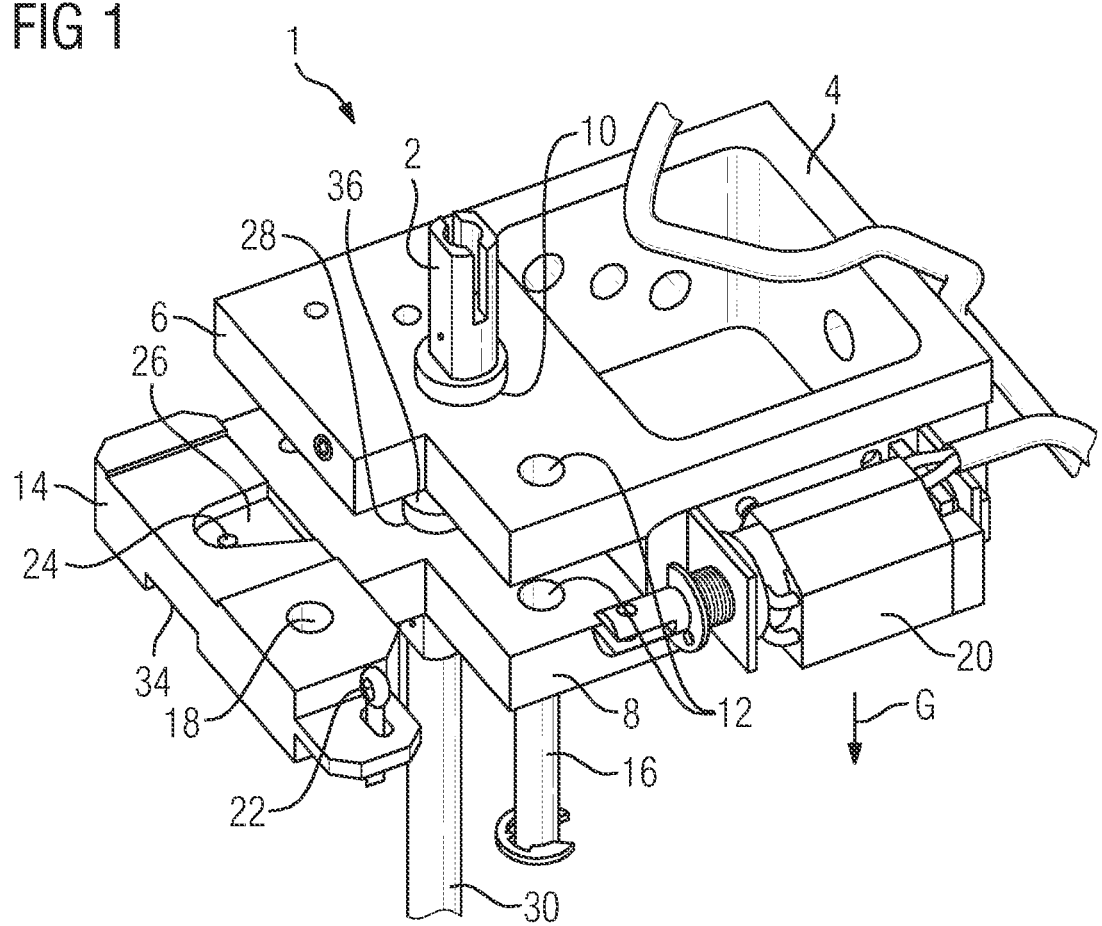

| | | | | |
|---|---|---|---|---|
| 3,637,065 | A | * | 1/1972 | Ruscitti .............. B65G 47/1485 198/396 |
| 3,874,564 | A | * | 4/1975 | Huneke ................ B65D 47/265 221/266 |
| 5,148,944 | A | * | 9/1992 | Kaufman .............. A61J 7/0084 221/131 |
| 5,493,865 | A | | 2/1996 | Wohlwend |
| 6,849,457 | B1 | | 2/2005 | Malyarov |
| 9,101,531 | B1 | * | 8/2015 | Song .................... A61J 7/0472 |
| 2012/0048861 | A1 | | 3/2012 | Filzinger |

FOREIGN PATENT DOCUMENTS

| | | | |
|---|---|---|---|
| EP | 0516111 A1 | 12/1992 | |
| EP | 0637741 A1 | 2/1995 | |
| EP | 0895950 A1 | 2/1999 | |
| EP | 0916457 A2 | 5/1999 | |
| EP | 2422879 A2 | 2/2012 | |
| FR | 2571348 A1 | 4/1986 | |
| JP | EP 0895950 A1 * | 2/1999 | ......... B65G 47/1485 |
| WO | WO 8300319 A1 * | 2/1983 | ......... B65D 83/0409 |

* cited by examiner

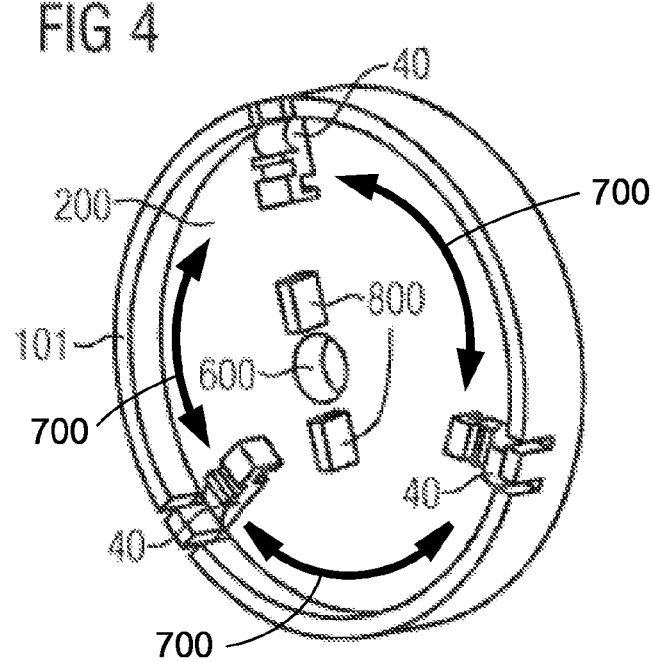
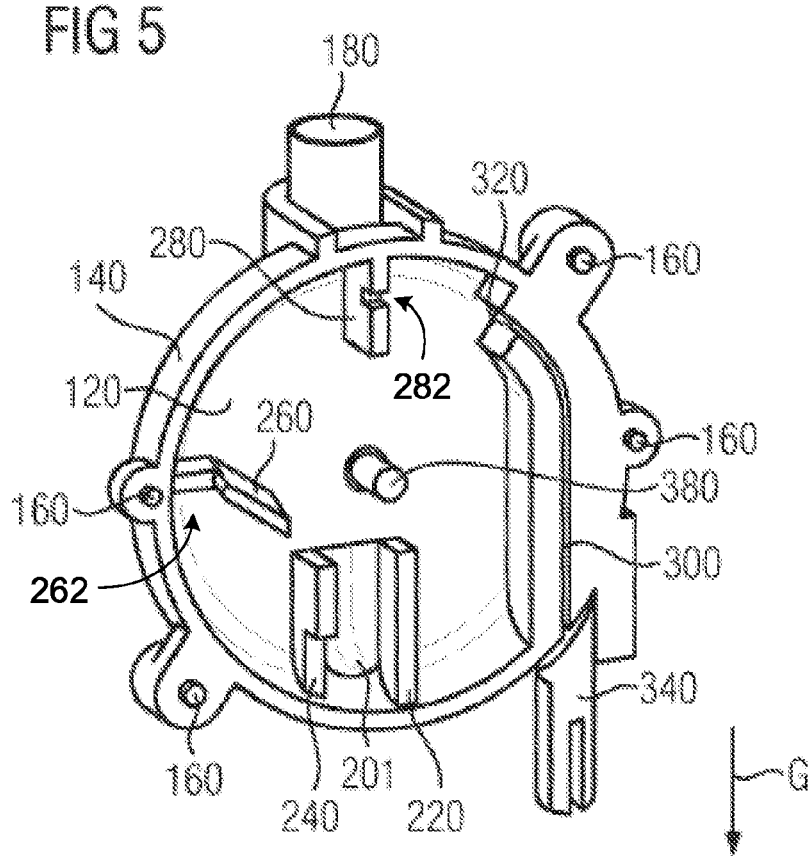

APPARATUS FOR SEPARATING SPHERICAL OR CYLINDRICAL OBJECTS

The invention relates to an apparatus for separating spherical or cylindrical objects, in general, and magnetically attractable agitating balls or agitating rods in an automatic analyzer, in particular.

Numerous testing and analyzing methods for determining physiological parameters in body-fluid samples such as blood, plasma, serum or urine or in other biological samples are nowadays carried out in automated fashion in appropriate analyzers.

Current analyzers are capable of carrying out a multiplicity of different test reactions and analyses using a multiplicity of samples. Common analyzers as used in clinical laboratories or in blood banks usually comprise a region for feeding sample vessels which contain the primary samples to be analyzed. A transporting system is usually provided in order to introduce the sample vessels into the analyzer, said system transporting the sample vessels, in the first instance, to a sample-identification device, by means of which sample-specific information which has been applied to a sample vessel is detected and passed on into a memory unit. The sample vessels are then transported to a sample-removal station. With the aid of a sample-pipetting device, there, at least one aliquot of the sample liquid is removed from the sample vessel and transferred to a reaction vessel.

The reaction vessels are usually disposable cuvettes, which are supplied in a cuvette container in the analyzer and are transferred automatically from the supply container to defined accommodating positions. The reagents which are necessary for providing different test-specific reaction mixtures are located in reagent containers, which are stored in a reagent station. The reagent containers are fed to the analyzer either automatically or manually.

Particularly popular measuring systems are those which are based on photometric, (e.g. turbidimetric, nephelometric, fluorometric or luminometric) or radiometric measuring principles. These methods allow the qualitative and quantitative detection of analytes in liquid samples without any additional separation steps having to be provided. Clinically relevant parameters such as, for example, the concentration or the activity of an analyte is frequently determined by an aliquot of a patient's body fluid being mixed simultaneously or successively with one or more test reagents in the reaction vessel, thus setting off a biochemical reaction which gives rise to a measurable change in an optical property of the test mixture.

The measurement result is passed on by the measuring system, once again, to a memory unit and evaluated. The analyzer then delivers sample-specific measured values to a user via an output medium, e.g. a monitor, a printer or a network connection.

Depending on the type of investigation carried out, it may be necessary for the liquid located in a reaction vessel to be subjected to thorough mixing. It may also be necessary for liquid reagents containing, for example, sedimenting constituents, e.g. particulate solid phases, to be subjected to thorough mixing. For this purpose, use is usually made of magnetic agitators. In this case, a magnet rotates at controllable speed beneath the appropriate reaction vessel or reagent container. The reaction vessel or reagent container contains a rod-like, usually cylindrical, or a spherical ferromagnetic agitating element, which is likewise made to rotate by the magnetic force of the rotating magnet and thus sets the liquid in the reaction vessel or reagent container in motion.

In the prior art, either the agitating elements are introduced into the reaction vessels manually by the user or the reaction vessels provided already contain one or more agitating elements.

On account of the multiplicity of tests which have to be carried out in an automatic analyzer, it is desirable for cuvettes to be charged in automated fashion with individual agitating elements.

For this purpose, it is possible for the agitating elements, in a first step, to be lined up in a row in the manner of a magazine, for example such that they are lined up in a row along their axis in a hose or tube. Either this can be carried out externally, in which case appropriate agitating-element magazines are inserted into the automatic analyzer, or the analyzer may itself comprise an apparatus which accommodates agitating elements in the form of bulk material and lines these up in a row in a hose in order to be removed individually.

In both cases, however, it has to be ensured that the agitating elements lined up in a row in the hose can be removed individually and fed reliably, in accordance with the requirements, to the respectively desired cuvettes.

It is therefore an object of the invention to provide an apparatus which allows quick and error-resistant separation of agitating elements and automated charging of cuvettes with the agitating rods.

This object is achieved according to the invention in that the apparatus comprises a lever provided with a bore, wherein the bore is configured such that is can accommodate an agitating element. The bore, in a first position of the lever, is arranged beneath an entry opening and, in a second position of the lever, is arranged above an exit opening, wherein the lever, in the second position, closes the entry opening.

The present invention therefore relates to an apparatus for separating rod-like or spherical objects, comprising a lever provided with a bore, wherein the bore is configured such that it can accommodate a rod-like or spherical object. The bore, in a first position of the lever, is arranged beneath an entry opening and, in a second position of the lever, is arranged above an exit opening, wherein the lever, in the second position, closes the entry opening.

An apparatus according to the invention is suitable for example in particular for separating rod-like or spherical agitating elements, such as agitating rods or agitating balls, or also for separating reaction vessels. The terms "objects" and "elements" should be understood as being synonymous.

It has been found that reliable separation is possible, in the first instance, by way of an accurately fitting holder for individual rod-like or spherical objects in the form of a corresponding bore which is shaped to match the objects. The bore here is arranged on a lever, in which case it can be moved. In the first position, one of the objects drops out of the hose into the bore. If the lever, when required to by the control unit, is moved into the second position, the exit of the hose is first of all closed, in which case it is not possible for any further object to follow on. The bore, in contrast, is moved over an exit opening, in which case the individual object drops out. A cuvette is arranged beneath the exit opening. The return movement of the lever causes the now emptied bore to pass beneath the hose again and a new object drops into the bore. This provides a straightforward and reliable mechanism for removing individual objects from the hose.

In an advantageous configuration, the lever is mounted in a floating manner on the apparatus, and the apparatus has a first centering means for centering the bore beneath the entry opening in the first position of the lever. The smallness of objects such as magnetic agitating rods or agitating balls in an automatic analyzer and the need for a high level of fitting accuracy of the bore mean that it is extremely difficult from a technical point of view to adjust the axis of rotation of the lever, if the latter is mounted in a fixed manner, such that the bore is always precisely centered beneath the entry opening. The production tolerances when the components are being made and assembled are typically too large here in order for such adjustment to be ensured in a reliable manner. Use should therefore be made of floating mounting, i.e. mounting with a predetermined small amount of play, in which case the position of the bore, when the lever reaches the first position, likewise has a certain amount of play. This should then provide a centering means which, for example by way of appropriate guidance, results in the bore being centered beneath the entry opening.

In analogous fashion, such a configuration is also advantageously provided in the second position. For this purpose, in an additional or alternative advantageous configuration, the apparatus has a second centering means for centering the bore above the exit opening in the second position of the lever. This also ensures a high level of fitting accuracy of the bore above the exit opening, in which case the objects drop reliably out of the bore.

A particularly straightforward configuration of the centering means is achieved by the latter having a circular-cylindrical elevation, which is arranged around the bore on the lever, and a wedge-shaped depression, which is arranged around the respective opening. If the circular elevation is guided into the tapering wedge as it is moved into the respective position, the symmetry means that, even in the case of different starting positions, it always passes into the same end position, in which case correct positioning is always ensured. For further optimization, it is also possible to round the wedge shape in the end region, in which case the wedge shape matches the shape of the circular elevation in the end position.

A further improvement in the level of fitting accuracy in particular in respect of the tolerances during production can be achieved by the respective elevation advantageously being the continuation of a circular-cylindrical sleeve, which encloses the respective opening. In other words: the entry opening and/or exit opening is located in a respective hollow-cylindrical sleeve which can be produced with comparatively small tolerances. The sleeve is arranged in an appropriate bore on the apparatus and projects beyond the periphery of the bore, this giving rise to the abovedescribed elevation.

The distance between the center point of the bore and the two edges of the depression advantageously corresponds to the radius of the elevation. The distance here is measured as the shortest stretch from the center point to a point on the edge. This gives rise to the desired precise adjustment of the bore above the exit opening and/or beneath the entry opening.

In an advantageous configuration, the apparatus comprises a magnetic actuating means assigned to the lever. Activation of the lever by means of an electromagnet can be realized in a technically straightforward manner and is comparatively quick. Floating mounting is made possible by the contactless transmission of force, since there is no need to make do here with any limitations in respect of movement.

The apparatus also advantageously comprises a filling-level sensor arranged above the entry opening. Said sensor may be configured, for example, in the manner of a light barrier. As a result, it is possible for the control device of the apparatus to determine whether there are sufficient objects stacked up in the supply chamber above the entry opening. If there are no objects present, a changeover can be carried out by the user in good time or more objects can be replenished from the bulk material.

The apparatus also advantageously comprises a sensor which is arranged beneath the exit opening and senses the through-passage of objects. This sensor, too, may be configured, for example, in the manner of a light barrier. As a result, the control device of the apparatus can determine whether an object is actually discharged when the lever is actuated. If an operational malfunction means that no object has been discharged, it is possible for the lever to be actuated, for example, anew. If no object has been discharged after a number of attempts, this is a sign, for example, that an object is jammed in the bore, and this can be indicated correspondingly to the user.

The present invention also relates to an automatic analyzer which comprises an abovedescribed apparatus for separating agitating elements, preferably magnetically attractable agitating rods or agitating balls.

The advantages achieved by the invention consist, in particular, in that, by virtue of agitating elements being separated from a stacked-up supply chamber by virtue of a straightforward lever with a bore, cuvettes can be charged in a particularly straightforward and reliable manner with agitating elements in an automatic analyzer. The apparatus is largely wear-free and functionally reliable.

In a further advantageous configuration, an apparatus according to the invention for separating rod-like or spherical objects is connected to an apparatus which accommodates magnetic agitating elements in the form of bulk material and lines these up in a row in a hose in order to be removed individually.

The present invention therefore also relates to an apparatus for separating magnetically attractable, rod-like or spherical elements, comprising a planar surface, which can be moved along a predetermined movement path and has at least one permanent magnet fitted on the rear side, and also comprising the following parts, which are arranged along the movement path and are in contact with the surface:
- a supply chamber for accommodating a quantity of magnetically attractable elements;
- a first chicane, having an aperture which corresponds to the cross section of the respective magnetically attractable element and is intended for stripping off surplus magnetically attractable elements;
- a channel, having an entrance and having a cross section for accommodating a magnetically attractable element, said cross section corresponding to the cross section of the respective magnetically attractable element;
- a hose, which is connected to the channel and of which the inner cross section corresponds to the cross section of the respective magnetically attractable element;

wherein an apparatus according to the invention for separating rod-like or spherical objects is fastened at the end of the hose.

The orientation of the hose advantageously has a directional component in the direction of gravity. This ensures that the magnetically attractable elements introduced into the hose and channel can drop downward automatically in the hose and be discharged individually there by means of an apparatus according to the invention for separating rod-like or spherical objects. There is no need for any active onward transportation.

The entrance of the channel is advantageously located in the movement path of the planar surface, and the longitudinal direction of the channel deviates from the movement path, in the plane of the surface, in a region which follows the entrance.

It has been found that the magnetic properties of the agitating elements can be utilized for separating purposes. For this purpose, in a first instance, a surface with a permanent magnet fitted on its rear side is guided, by appropriate mechanical guidance, past a supply chamber containing a multiplicity of magnetically attractable elements, in which case a multiplicity of the same type of agitating elements remain adhering magnetically to the surface. As a result of the magnetic field strengthening in the direction of the source, typically one agitating element, typically in the form of a ball or of a rod, will assume a position above the permanent magnet and orient itself, in addition, in accordance with the north/south polar orientation of the magnet. In addition, typically further agitating elements from the supply chamber will remain adhering to the surface in a chaotic or only partially ordered arrangement. These are stripped off by virtue of the surface being moved over a chicane with an aperture corresponding to the cross section of the respective type of agitating element, in which case just a single agitating element remains, or possibly two agitating elements arranged longitudinally one behind the other remain, on the surface. By virtue of the surface being moved over a channel of a cross section corresponding to the cross section of the respective type of agitating element, said agitating elements are introduced into the channel. If the surface is then moved laterally beyond the periphery of the channel, which can be brought about either by a change in the movement direction of the surface or by curvature of the channel, the agitating element or elements is or are moved laterally on the surface until it/they passes/pass out of the region of influence of the permanent magnet. The agitating element or elements is/are then located in the channel in a state in which it/they is/are lined up in a row.

In a particularly straightforward configuration, the surface moves along a circular path and the poles of the permanent magnet are oriented tangentially. This allows the surface to be moved by straightforward rotation by an electric motor, which makes the method easier to implement. Tangential orientation of the magnet means that the agitating elements are oriented automatically in the movement direction.

In a further advantageous configuration, the method steps are repeated cyclically and the agitating elements located in the channel are guided into the hose, of which the inner cross section corresponds to the cross section of the respective type of agitating element. In particular if movement takes place along a circular path, cyclic repetition can be implemented in a particularly straightforward manner. New agitating elements are removed from the supply chamber at regular intervals here. If said agitating elements are guided into the hose of the appropriate diameter, they are located there in a state in which they are lined up in a row and they can be discharged individually at the end of the hose by means of an apparatus according to the invention for separating rod-like or spherical objects.

A multiplicity of magnetically attractable agitating elements of the same shape and size, and therefore of the same nature, belong to a single type of agitating element.

In an advantageous configuration, the movement path is a circular path, the planar surface and the circular path are located in a single plane, and the poles of the permanent magnet are oriented tangentially.

The planar surface is advantageously part of a circular plate. This gives the advantage of the possibility of forming a closed system: the supply chamber, first chicane and channel are arranged in circular form in a round trough, and the circular plate is fitted thereon in a rotatable manner, in the form of a lid, with the magnets on the outside. All that is required is for an introduction opening for the magnetically attractable elements and an exit for the magnetically attractable elements deposited in the channel to be provided. Separation takes place entirely within the closed space.

In a further advantageous configuration, the circular plate, on its rear side, has a plurality of permanent magnets on a circular path. This makes it possible to accelerate the separation process without increasing the rotational speed of the circular plate, since a plurality of magnetically attractable elements can be introduced into the channel per revolution of the circular plate.

The apparatus advantageously comprises a second chicane, which is arranged along the movement path, is in contact with the surface and has an aperture which is larger than that of the first chicane. Such a second chicane with a larger through-passage opening is arranged upstream of the first chicane, as seen in the movement direction, and acts in the manner of a coarse filter, which, prior to all but one magnetically attractable element being stripped off, in the first instance removes most of the surplus elements. This is because, if an excessive number of elements is carried along by the plate, tilting may occur, or the elements closest to the magnet are arranged in chaotic fashion, in which case possibly all the elements are stripped off. This is prevented by a relatively large aperture located upstream.

Figure 2:
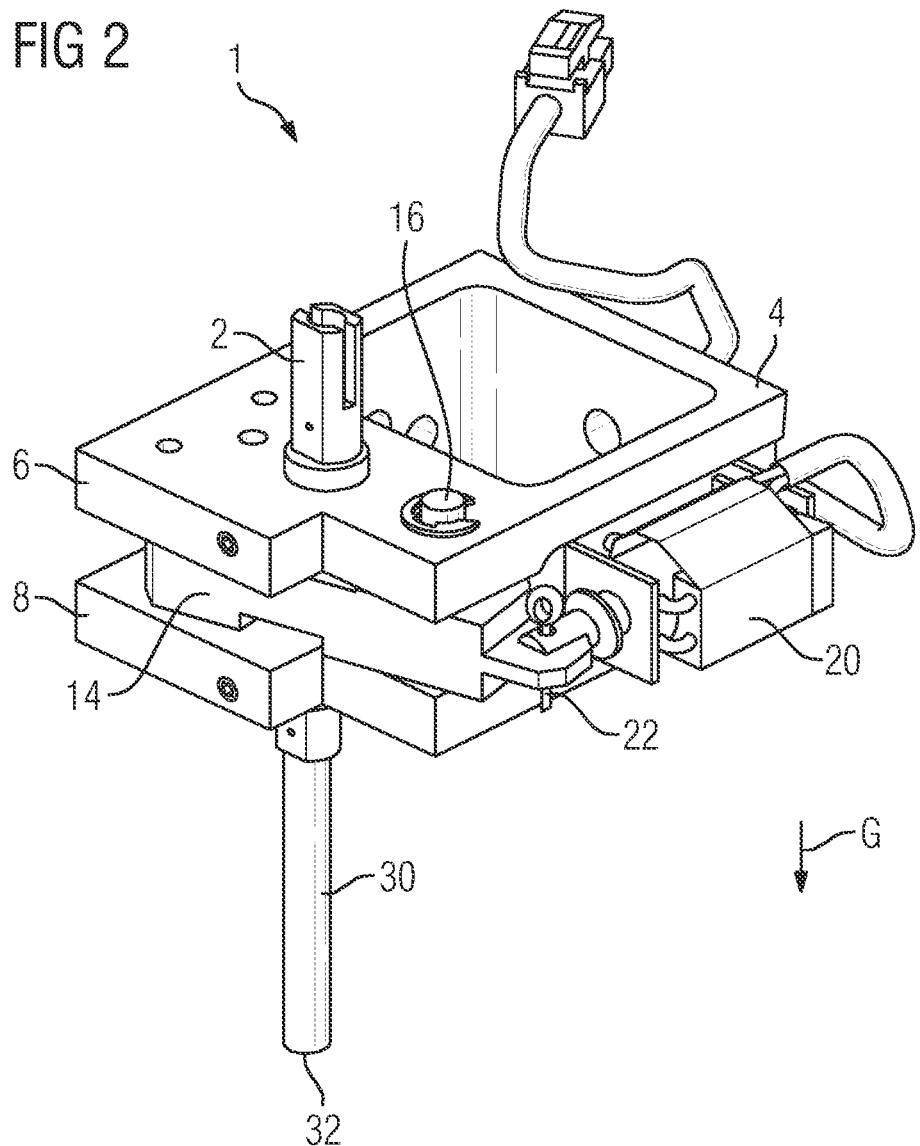
Figure 3:
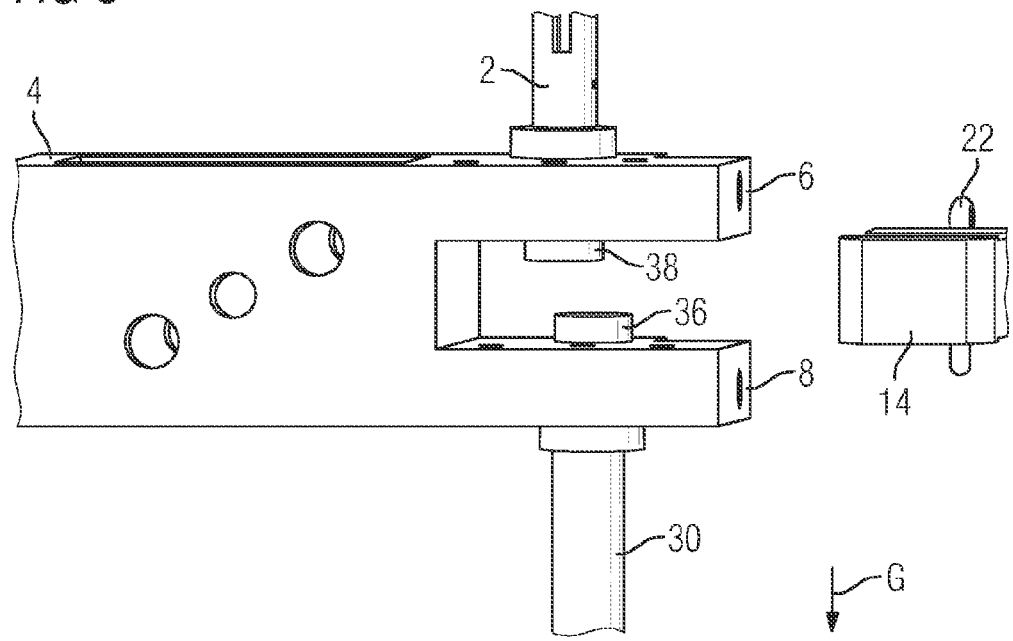
Figure 6:
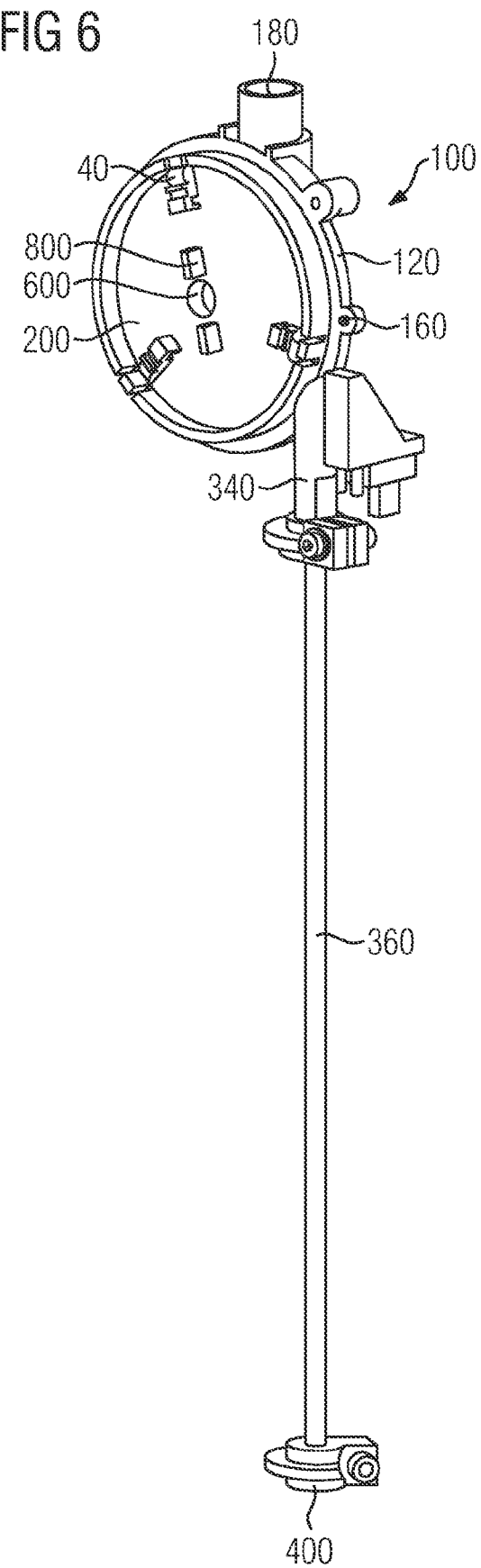

The invention will be explained in more detail with reference to a drawing, in which:

FIG. 1 shows an apparatus (1) according to the invention with a lever, for removing agitating elements individually from a hose, in a non-fitted state, FIG. 2 shows the lever in the fitted state, and FIG. 3 shows another view of the non-fitted lever from FIG. 2, FIG. 4 shows a circular plate with a magnet fitted on its rear side, FIG. 5 shows a trough which can be closed by the circular plate and has a supply chamber for agitating elements, and also has chicanes and a channel, and FIG. 6 shows the assembled apparatus (100) with circular plate, trough and connected hose.

Like parts are provided with the same designations throughout the figures.

FIGS. 1 to 3 explain the individual parts of an apparatus 1 for separating agitating elements in an analyzer (not illustrated specifically). The agitating elements, which are to be separated by the apparatus 1 and discharged into reaction vessels, are cylindrical and have a length of 4 mm and a diameter of 1 mm. They are produced from a ferromagnetic material and are fed in the form of bulk material to the automatic analyzer. Here, they are guided, by an apparatus which is not illustrated specifically, into a hose (not illustrated either), of which the internal diameter corresponds to the diameter of the agitating elements, in which case the agitating elements slide downward along the hose and are lined up in a row in the hose. The agitating elements are also referred to hereinbelow as agitating rods.

The hose is flexible and, depending on the installation situation, can be appropriately lengthened or shortened. A fastening means is arranged at the exit of the hose and is connected to the sleeve 2, which is shown in FIG. 1. The sleeve 2 is of essentially hollow-cylindrical configuration and has a fastening device for the hose. The internal diameter in the lower part of the sleeve 2 corresponds to that of the hose. The agitating rods thus exit from the hose and stack up in the sleeve 2, which is therefore also referred to as an introduction sleeve.

The part which is shown in FIG. 1 comprises, in the first instance, a central fastening frame 4, from which extend two plane-parallel, horizontally oriented plates 6, 8. The fastening frame 4 and plates 6, 8 are configured in one piece. The upper plate 6 comprises a bore 10, in which the sleeve 2 is arranged. The sleeve 2 here exits on the other side of the upper plate 6, to form an elevation 38, which is shown in FIG. 3 and will be described in more detail hereinbelow.

Offset horizontally in relation to the sleeve 2, concentric bores 12 for mounting a lever 14 by means of a bolt 16 are provided in the plates 6, 8. The lever 14 is mounted in a floating manner here by having a slot 18 through which the bolt 16 passes. The slot 18 allows the mounting to have an amount of play. A magnetic switch 20, arranged on the fastening frame 4, is connected to the lever 14 via a split pin 22 such that it can actuate the lever 14.

The lever 14 here is moved by the magnetic switch 20 between a first position and a second position. The movement is controlled by a control device of the automatic analyzer. The lever 14 has a bore 24 which, in the first position, is located beneath the introduction sleeve 2. The diameter of the bore 24 corresponds to that of an agitating rod. The height of the bore 24 corresponds approximately to a length of an agitating rod. On the upper side of the lever 14, a depression 26 is arranged around the bore 24.

The lower plate 8 likewise has a bore 28, into which is connected a downwardly extending hollow-cylindrical sleeve 30 with an exit opening 32, which is shown in FIG. 2. The bore 28 is arranged offset in relation to the bore 10 of the sleeve 2 in the upper plate 6. In a manner analogous to the sleeve 2, however, the sleeve 30 likewise extends into the interspace between the plates 6, 8, in which case a circular-cylindrical elevation 36 forms here. The bore 24 in the lever 14, in the second position of the lever 14, is arranged above the sleeve 30.

On the underside of the lever 14, a depression 34, designed in a manner analogous to the depression 26, is arranged around the bore 24. The depression 34 is likewise configured in the form of a wedge with a rounded tip, although the opening direction of the wedge here is oriented in the opposite movement direction of the lever 14.

The respective depressions 26, 34 are configured as follows in relation to the elevations 38, 36 formed by the sleeves 2, 30: the rounded tips of the wedges have the same radius as the elevations 38, 36. Following the tips, the edges of the respective wedge become further spaced apart. If, therefore, the lever 14 is moved horizontally into the respective depression 26, 34, the elevation 38, 36 is centered automatically in the rounded tip of the wedge.

The apparatus 1 shown in FIG. 1 is shown in the assembled state in FIG. 2. FIG. 3 shows, once again, the exploded drawing from FIG. 1, this time in a horizontal view. It is possible to see here the offset of the sleeves 2, 30 and the associated elevations 36, 38. The exit opening for the agitating rods is centered in the elevation 36 of the sleeve 30, and the entry opening is centered in the elevation 38 of the sleeve 2, the agitating rods being stacked above said entry opening and dropping gradually into the bore 24.

The resulting centering action will be explained once again: in the form of the elevations 36, 38 the sleeves 2, 30 extend into the region between the plates 6, 8. The circular-cylindrical elevations 36, 38 engage in the depressions 26 and 34. The depressions 26, 34 here are in the form of oppositely directed wedges. The lever 14 is mounted in a floating manner by the slot 18, i.e. in respect of its axis, it is fixed with an amount of play only within certain predetermined limits. As a result of the wedge shape of the depressions 26, 34, then, in each end position of the lever 14, engagement in the elevations 36, 38 results in automatic, highly precise centering, in which case the agitating rods can drop through without jamming.

The functioning of the apparatus 1 will be explained with reference to FIGS. 1 to 3: in the rest state, the lever 14 is located in the first position. The agitating rods guided into the hose drop downward. One of the agitating rods drops out of the sleeve 2 into the bore 24. It rests here on the elevation 36 of the sleeve 30. The rest of the agitating rods in the hose or within the sleeve 2 stack above the agitating rod located in the bore 24.

If, then, an agitating rod is delivered into a cuvette from the exit opening 32, the control unit activates the magnetic switch 20. The latter moves the lever 14 into the second position. The bore 24 is then located above the sleeve 30, and the agitating rod drops downward. The lever 14, in this position, closes the entry opening of the introduction sleeve 2, in which case it is not possible for any following agitating rod to drop down. It is only following return movement into the first position, when the bore 24 is located beneath the sleeve 2, that a further agitating rod can follow on into the bore 24.

Sensors (not illustrated specifically) configured in the manner of a light barrier are arranged in the region of the sleeve 2 and of the sleeve 30. The sensor in the sleeve 2 monitors the filling level of the sleeve 2, i.e. whether there is still a sufficient supply of agitating rods available. If the lever 14 is actuated, the control unit checks, by means of the sensor in the sleeve 30, whether an agitating rod has been discharged. If this is not the case, the lever is actuated anew. If no agitating rod is discharged after a number of attempts, a malfunction has occurred and a user alarm is triggered.

FIGS. 4 to 6 explain the individual parts of an apparatus 100 for separating agitating elements in an analyzer (not illustrated specifically). The agitating elements, which are to be separated by the apparatus 100 and discharged into reaction vessels, are cylindrical and have a length of 4 mm and a diameter of 1 mm. They are produced from a ferromagnetic material and are fed in the form of bulk material to the automatic analyzer. The agitating elements are also referred to hereinbelow as agitating rods.

FIG. 4 shows a circular plate 200 which serves to accommodate, and separate, agitating rods by means of permanent magnets 40. FIG. 4 shows a rear-side view of the circular plate 200, which, with the exception of a center-point bore 600 for a drive shaft, is of fully planar configuration on the side which is not illustrated in FIG. 4. On the rear side shown, drivers 800, for the purpose of fastening a drive shaft, are arranged in the region of the bore 600. The three permanent magnets 40 are arranged on the rear side on a circular predetermined movement path 700 around the bore 600. They form an equilateral triangle and have their north/south pole axis arranged tangentially on the circular path 700. The circular plate 200 also has an elevated encircling periphery 101, which is interrupted merely by retaining means for the permanent magnets 40.

FIG. 5 shows a disk-like trough 120 with an encircling elevated periphery 140. Various fixing pins 160 for fixing the apparatus 100 in an accurately fitting manner in the automatic analyzer are arranged on the outside. FIG. 5 shows the disk-like trough 120 in that orientation in relation to gravitational force G which is preferred for the apparatus 100. The trough 120 is closed by the circular plate 200, which is shown in FIG. 4, such that the planar side of the circular plate 200 is oriented toward the interior of the trough 120 and forms a closed cavity. Accordingly, the periphery 140 has the same diameter as the circular plate 200 and is flat. All the internals in the trough 120, these being explained hereinbelow, likewise extend up to the level of the periphery 140, in which case they are in contact with the circular plate 200 unless described specifically to the contrary.

The trough 120, on its upper side, has an introduction opening 180 for agitating rods. The agitating rods drop downward in a channel on the rear side of the trough 120. In the region of the bottom periphery 140, the channel is curved forward and connected to the interior of the trough 120. A supply chamber 201 which is intended for accommodating a multiplicity of agitating rods, and is bounded by vertical walls with restraining ribs 220, 240, forms here. The rear-side channel thus forms, in the manner of a riser tube, a means for introducing the agitating rods which prevents the trough 120 from being filled up completely; rather, only a certain quantity of agitating rods is supplied within the trough 120 and, at the same time, leaves space within the trough 120 for the separating method described hereinbelow.

The right-hand restraining rib 220 is not in contact with the circular plate 200, in which case individual agitating rods can pass through. The left-hand restraining rib 240 extends as far as the circular plate 200, but has, at its lower end, an aperture which ensures that agitating rods can pass through. The aperture covers the radius of the circular path on which the permanent magnets 40 are arranged.

An obliquely downwardly oriented wall with a chicane 260 formed in the manner of an edge is arranged on the left-hand side of the trough 120. The chicane 260 has an aperture 262 which covers the radius of the circular path 700 on which the permanent magnets 40 are arranged and does not extend as far as the circular plate 200. The aperture 262 is smaller than the aperture of the left-hand restraining rib 240, but still large enough to allow a plurality of agitating rods to pass through at the same time.

A vertically arranged further wall with a chicane 280 configured in the manner of an edge is provided at the upper end of the trough 120, the chicane 280 having an aperture 282 which is located precisely on the circular path 700 on which the permanent magnets 40 are arranged, and the diameter of the aperture 282 being only slightly larger than the diameter of an agitating rod. The aperture 282 allows only a single agitating rod, or two agitating rods arranged longitudinally one behind the other, to pass through.

A channel 300 bounded by walls is arranged on the right-hand side of the trough 120. The wall which is directed toward the periphery 140 extends further upward than the wall which is directed away from the periphery 140. The channel 300 is adapted in terms of diameter and depth to the diameter of the agitating rods. The entrance 320 of the channel 300 is located on the circular path of the permanent magnets 40. The channel 300 initially follows said circular path, until, finally, it leads vertically downward.

The channel 300 is followed by a connection 340 for the hose 360, which is shown for the first time in FIG. 6. The walls described do not extend as far as the center point of the trough 120, in which case a free space remains here, this containing just one essentially cylindrical bearing journal 380 with a bore for a drive shaft.

FIG. 6 shows the circular plate 200 fastened on the trough 120 and having the abovedescribed parts and the hose 360.

The functioning of the apparatus 100 will now be explained with reference to FIGS. 4 to 6: as seen from the point of view of FIG. 5, the circular plate 200 is rotated in the clockwise direction via a drive shaft (not illustrated specifically) with an electric motor. If a permanent magnet 40 passes through the supply chamber 201, the magnetic force means that a multiplicity of agitating rods remain adhering to the planar surface of the circular plate 200. The agitating rods are carried along in the clockwise direction. Surplus agitating rods are gradually stripped off at the restraining rib 240 and the chicane 260 and drop downward. At the latest following the chicane 260, one of the agitating rods should have assumed a preferred position directly above the respective permanent magnet 40 on account of the action of force of the magnetic field, which decreases with distance. It is also possible for two agitating rods arranged longitudinally one behind the other to assume this position.

Finally, all but the one or the two agitating rods in the preferred position are stripped off at the chicane 280 and drop back into the supply chamber 201. The remaining agitating rod or rods is or are introduced into the channel 300. As soon as the agitating rods reach the vertical portion of the channel 300, the permanent magnet 40 moves away from the channel 300 on the circular path. The agitating rods in the channel 300 cannot follow the permanent magnet 40, on account of the form fit, and are thus removed from the region of action of the permanent magnet 40. They subsequently drop into the hose 360.

The circular plate 200 revolves continuously. The method described is carried out three times, as a result of three permanent magnets 40 being used, per revolution. A sensor (not illustrated specifically) is arranged at the connection 340 and senses the through-passage of agitating rods. The control unit (not shown specifically) is designed such that, if no agitating rods are sensed over three revolutions, the drive motor is stopped and moved in the opposite direction for one revolution. Thereafter, operation transfers back to normal again. This makes it possible to eliminate any jamming of the agitating rods in the interior of the trough 120.

The hose 360 is flexible and, depending on the installation situation, can be appropriately lengthened or shortened and arranged in place. Sensors (not illustrated specifically) designed in the form of light barriers are arranged at the connection 340 and the exit 400 of the hose. The sensors serve for detecting the filling level of the hose 360 and make it possible for the control unit to check the correct functioning of the unit made up of the circular plate 200 and trough 120. If, for example, after a predetermined number of revolutions of the circular plate 200, there is no through-passage of agitating rods detected at the connection 340, this indicates a malfunction, e.g. jamming of agitating rods in the trough 120. It is possible here for the jamming to be released for example by automatically induced rotation of the circular plate 200 in the opposite direction. Should it not be possible to eliminate the malfunction, a user alarm is triggered.

Provision is made for the apparatus 1 according to the invention to be fastened at the exit 400.

| LIST OF DESIGNATIONS | |
|---|---|
| 1, 100 | Apparatus |
| 2 | Sleeve |
| 4 | Fastening frame |
| 6, 8 | Plate |
| 10, 12, 24, 28, 600 | Bore |
| 14 | Lever |

-continued

LIST OF DESIGNATIONS

| 16 | Bolt |
|---|---|
| 18 | Slot |
| 20 | Magnetic switch |
| 22 | Split pin |
| 26 | Depression |
| 30 | Sleeve |
| 32 | Exit opening |
| 34 | Depression |
| 36, 38 | Elevation |
| 100 | Apparatus |
| 200 | Circular plate |
| 40 | Permanent magnet |
| 800 | Driver |
| 101 | Periphery |
| 120 | Trough |
| 140 | Periphery |
| 160 | Fixing pin |
| 180 | Introduction opening |
| 201 | Supply chamber |
| 220, 240 | Restraining rib |
| 260, 280 | Chicane |
| 300 | Channel |
| 320 | Entrance |
| 340 | Connection |
| 360 | Hose |
| 380 | Bearing journal |
| 400 | Exit |
| G | Gravity |

The invention claimed is:

1. An apparatus for separating rod-like or spherical objects, comprising a lever provided with a bore, wherein the bore is configured such that it can accommodate a rod-like or spherical object, and wherein the bore, in a first position of the lever, is arranged beneath an entry opening in a first orientation and, in a second position of the lever, is arranged above an exit opening in the same first orientation, wherein the lever, in the second position, closes the entry opening, the lever rotatably mounted on the apparatus, the apparatus further having a first centering element for centering the bore beneath the entry opening in the first position of the lever, wherein the first centering element has a first circular-cylindrical elevation arranged around the bore on the lever and has a first wedge-shaped depression arranged around the entry opening.

2. The apparatus as claimed in claim 1, wherein the apparatus has a second centering element for centering the bore above the exit opening in the second position of the lever.

3. The apparatus as claimed in claim 2, wherein the first centering element is on a first side of the lever and the second centering element is on a second, opposite side of the lever.

4. The apparatus as claimed in claim 3, wherein:
the second centering element has a second circular-cylindrical elevation, which is arranged around the bore on the lever, and a second wedge-shaped depression, which is arranged around the exit opening and is oriented in an opposite movement direction of the lever than the first wedge-shaped depression.

5. The apparatus as claimed in claim 1, wherein the circular-cylindrical elevation is a continuation of a circular-cylindrical sleeve, which encloses the entry opening.

6. The apparatus as claimed in claim 1, wherein a distance between a center point of the bore and two edges of the wedge-shaped depression corresponds to a radius of the circular-cylindrical elevation.

7. The apparatus as claimed in claim 1, comprising a magnetic switch connected to the lever.

8. The apparatus as claimed in claim 7, comprising a filling-level sensor arranged above the entry opening.

9. The apparatus as claimed in claim 8, comprising a sensor which is arranged beneath the exit opening and senses a through-passage of rod-like or spherical objects.

10. The apparatus as claimed in claim 1, wherein the first orientation is a vertical orientation.

11. An apparatus for separating magnetically attractable, rod-like or spherical elements that can be moved along a predetermined movement path, the apparatus comprising a planar surface and having at least one permanent magnet fitted on a rear side of the planar surface, the apparatus also comprising:
a supply chamber for accommodating a quantity of magnetically attractable elements;
a first chicane, having an aperture which corresponds to a cross section of one of the magnetically attractable elements and is intended for stripping off surplus magnetically attractable elements;
a channel, having an entrance and having a cross section for accommodating a magnetically attractable element, said cross section corresponding to the cross section of the respective magnetically attractable element;
a hose, which is connected to the channel at a first end of the hose and of which an inner cross section corresponds to the cross section of one of the magnetically attractable elements; and
an apparatus as claimed in claim 1 fastened to a second end of the hose.

12. An automatic analyzer having an apparatus as claimed in claim 11 and a plurality of the magnetically attractable, rod-like or spherical elements.

13. The apparatus as claimed in claim 11, wherein an orientation of the hose has a directional component in a direction of gravity.

14. The apparatus as claimed in claim 13, wherein the movement path is a circular path, the planar surface and the circular path are located in a single plane, and poles of the permanent magnet are oriented tangentially.

15. The apparatus as claimed in claim 14, wherein the planar surface is part of a circular plate.

16. The apparatus as claimed in claim 15, wherein the circular plate, on its rear side, has a plurality of permanent magnets on a circular path.

17. The apparatus as claimed in claim 11, comprising a second chicane, which is in contact with the planar surface, is arranged along the movement path between the supply chamber and the first chicane, and has a larger aperture than the aperture of the first chicane.

18. A method of using an apparatus as claimed in claim 11, for separating magnetically attractable, spherical or rod-like agitating elements in an automatic analyzer, comprising:
receiving one of the rod-like or spherical elements from the hose into the bore of the lever;
rotating the lever from the first position to the second position; and
discharging the rod-like or spherical elements into the exit opening.

* * * * *